(12) United States Patent
Altshuler et al.

(10) Patent No.: US 6,197,516 B1
(45) Date of Patent: Mar. 6, 2001

(54) COMPUTER METHOD AND APPARATUS FOR ANALYZING MUTATIONS IN DNA

(75) Inventors: David Altshuler, Brookline; Eric S. Lander, Cambridge, both of MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/309,328

(22) Filed: May 11, 1999

Related U.S. Application Data

(60) Provisional application No. 60/085,118, filed on May 12, 1998.

(51) Int. Cl.$^7$ .................................................. C12Q 1/68
(52) U.S. Cl. ............................ 435/6; 435/6; 536/25.4; 536/23.1; 935/78; 935/77; 210/635; 210/656; 210/659; 210/198.2; 204/480; 204/456; 204/182.8
(58) Field of Search ................................ 435/6; 536/25.4, 536/23.1; 935/78, 77; 210/635, 656, 659, 198.2; 204/450, 456, 182.8

(56) References Cited

U.S. PATENT DOCUMENTS

| | | | |
|---|---|---|---|
| 3,826,905 | * | 7/1974 | Vallkama et al. ................ 235/151.2 |
| 5,585,236 |   | 12/1996 | Bonn et al. ........................... 435/5 |
| 5,795,976 | * | 8/1998 | Oefner et al. ..................... 536/25.4 |

OTHER PUBLICATIONS

Huber, C.G., et al., "High–resolution liquid chromatography of DNA fragments on non–porous poly(styrene–divinylbenzene) particles," *Nucleic Acids Research*: 21(5), pp. 1061–0166 (1993).

Underhill, P.A. et al., "Detection of Numerous Y Chromosome Biellelic Polymorphisms by Denaturing High–Performance Liquid Chromatography," *Genome Research*, 7:996–1005 (1997).

DHPLC Workshop, Stanford University, CA; Mar. 17, 1997 (pp. 32–43).

Leonard Lerman's Lab Members; Cathy Hogan, Jeremy Lambert and Leonard Lerman, http://web/mit.edu/biology/dna, downloaded Mar. 4, 1999.

\* cited by examiner

*Primary Examiner*—W. Gary Jones
*Assistant Examiner*—Janell Taylor
(74) *Attorney, Agent, or Firm*—Hamilton, Brook, Smith & Reynolds, P.C.

(57) ABSTRACT

The present invention provides a computer method and apparatus for detecting mutations in DNA fragments. Specifically, percent acetonitrile and threshold temperature, for use in the denaturing high performance liquid chromatography method of separating DNA fragments, are determined. In a preferred embodiment, the present invention serves as a preprocessor to the DHPLC system described in the cited art.

14 Claims, 8 Drawing Sheets

COMPUTER METHOD AND APPARATUS FOR ANALYZING MUTATIONS IN DNA

RELATED APPLICATION(S)

This application claims the benefit of U.S. Provisional application No. 60/085,118 filed on May 12, 1998, the entire teachings of which are incorporated herein by reference.

BACKGROUND OF THE INVENTION

Detection of a mutation in a DNA fragment is important for many reasons, for example determining the existence of disease, malfunction or abnormality in an animal or human organism. By way of background, DeoxyriboNucleicAcid (DNA) is the chemical inside the nucleus of a cell that carries the genetic instructions, or code, for making living organisms.

DNA comprises two long, molecular strands lying side by side in a double spiral referred to as a double helix. The double helix structural arrangement of DNA looks something like a long ladder twisted into a coil. The sides of the "ladder" are formed by sugar and phosphate molecules, and the "rungs" are made of a large number of chemical building-blocks called bases, with a pair of bases forming the rung. The bases are referred to by the code letters A, T, G and C which stand for the chemicals adenine, thymine, guanine, and cytosine, respectively. At each end of a rung are complementary bases (i.e. the "base pair") which form the bond between the two strands forming the DNA. In base pairing, adenine (A) always pairs with thymine (T), and guanine (G) always pairs with cytosine (C). That is, if on one side of the ladder rung there is an A, the base on the other side of the ladder rung is a T, and if one end of the rung is a G, the opposite end is a C. As a result, the two strands of the DNA structure are inverted copies of each other.

Although there are only four different kinds of bases, the order in which they appear along the strand of DNA dictate the genetic code of an organism. A DNA strand can therefore be referred to by its unique sequence of letters commonly called a DNA sequence. The effort of determining the exact order of the base pairs in a segment of DNA is referred to as DNA sequencing.

The strength of the bond between the two strands of the DNA structure is subject to several factors. One factor is the length of the DNA fragment. Longer fragments possess a stronger bond between the strands than shorter fragments. In addition, the specific sequence order of the fragment has an effect on the strength of the bond. That is, a strand sequence of GGGAAATTT has a different bond strength than a strand sequence of GATGATGAT. A third factor in bond strength is the actual bond pair itself. Bonds formed between Gs and Cs are stronger than bonds formed between As and Ts A mutation is a permanent structural alteration in DNA. These mutations in some cases may have no effect on the organism however, in some instances they may cause disease, malfunction or abnormality in the organism. Accordingly, it is beneficial to identify such mutations as well as to determine whether an identified mutation exists in a particular individual.

A method for determining the existence of a mutation has evolved where a DNA fragment is exposed, for a period of time, to a threshold temperature, specific to that DNA fragment, which forces the two strands of the DNA apart, breaking the bond between the base pairs. The percent of the strand pair which is split apart at different moments in time, is referred to as the percent melted (or fraction single stranded).

A copy of a "good" (mutation-free) DNA fragment is typically made using a process called polymerase chain reaction (PCR). This "good" DNA fragment is separated and each strand is annealed with a strand from a DNA fragment which includes a mutation, the strands of which have also been separated. As mentioned above, the two strands of a DNA structure should be inverted copies of each other. When the series of bases on one copy of the DNA fragment do not match the series of bases on the other copy of the pair, a "mutation" is said to exist. Where a mutation in the DNA structure exists, the bond between the two strands is weakened. In the instance where a mutation exists within a strand, the percent melted at a specific period of time will differ from that if the strand had no mutations. A number of analytic separation methods can be used to detect differences in double stranded character of DNA.

The threshold temperature for analyzing a given DNA fragment for mutations is dependent on the length of the fragment as well as the specific fragment sequence. As described above, the length, base pairing and sequence order of the DNA fragment are each determinative of the strength of the bond and are, therefore, factors in determining the amount of heat required to separate the strands of the DNA fragment.

Historically, more is known about the separation of DNA fragments than is known about specific mutations. The separation of DNA fragments using chromatographic techniques has been studied and reported on by Peter Oefner and colleagues. See "High Resolution Liquid Chromatography of DNA Fragments on Non-Porous Poly(styrene-divinylbenzene) Particles", *Nucleic Acids Research*, Volume 21, No. 5, pages 1061–1066 (1993). In U.S. Pat. No. 5,585,236 to Bonn et al., an improved chromatographic technique for separating nucleic acids is disclosed. More recently, Oefner disclosed the exploitation of the chromatographic separation technique for mutation detection in a "DHPLC Workshop" at Stanford University, California, Mar. 17, 1997. By that time, the chromatographic technique was referred to and known as DHPLC (Denaturing High Performance Liquid Chromatography). A specific example of the DHPLC technique for detection of Y chromosomes in biallelic polymorphisms is given by Peter A. Underhill et al., "Detection of Numerous Y Chromosomes Biallelic Polymorphisms by Denaturing High Performance Liquid Chromatography", *Genome Research* 7:996–1005 (1997). Also see, Oefner, P. J. and Underhill, P. A. U.S. Pat. application, Ser. No. 08/512,681, "Detection of DNA Heteroduplex Molecules by Denaturing High-Performance Liquid Chromatography and Methods for Comparative Sequencing", filed on Aug. 8th, 1995.

Briefly summarizing the DHPLC method for separating DNA strands, a straw-like apparatus, referred to as a separation column, is adjusted to a specific concentration of acetonitrile solution and a specific temperature. A DNA fragment is prepared from a given individual, typically using PCR which provides multiple copies of a piece of DNA. The DNA fragments are injected onto the column and adhere. The concentration of the acetonitrile solution is gradually increased and the elution rate of the DNA fragments is monitored. Typically, the process is repeated for the same fragment from multiple individuals and the patterns of elution of the DNA fragments over time are compared. For those individuals whose DNA includes a mutation, a lower concentration of acetonitrile will cause an amount of the DNA to strip from the column than for those individuals whose DNA samples do not include a mutation.

Accordingly, in the various foregoing disclosures of the DHPLC technique, there are two conditions which must be specified by the user in order to analyze any specific DNA fragment: (1) temperature and (2) percent acetonitrile, which is the solution used by the chromatography column. In the current publications, the key or threshold operating temperature used for the chromatography columns is assumed as a given value or, at most, described as being empirically determined. That is, multiple DNA test fragments are studied under a range of operating temperatures. After much experimentation, a viable temperature is determined. See page 1003, right hand column of Underhill, et al. Such empirical determination is often inexact, time consuming and laborious.

SUMMARY OF THE INVENTION

The present invention provides automated means for determining percent acetonitrile and threshold temperature for use in the denaturing high performance liquid chromatography method of separating DNA fragments as disclosed in the above-mentioned references. In particular, the present invention provides a computer method and apparatus for determining a temperature and solution concentration at which mutations can be detected in a subject DNA fragment. In a preferred embodiment, the present invention serves as a preprocessor to the DHPLC system described in the cited art.

In further detail, method and apparatus are provided for deriving, from a threshold temperature calculated for a gel electrophoresis process, the operating temperature at which strands of a DNA fragment become partially separated in a DHPLC process. A concentration of a solution for the DHPLC process is also calculated, both the solution concentration and temperature being calculated from an input string comprising a DNA fragment sequence.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The present invention provides an automated technique to detect mutations in a DNA fragment. Specifically, an operating temperature and acetonitrile concentration are provided by automated means from a DNA fragment sequence, thus eliminating the experimentation required by the prior solutions to identify such quantities. In addition, the current invention provides a system which enables parallel testing of DNA fragments thus promoting efficient usage of time.

Figure 1:
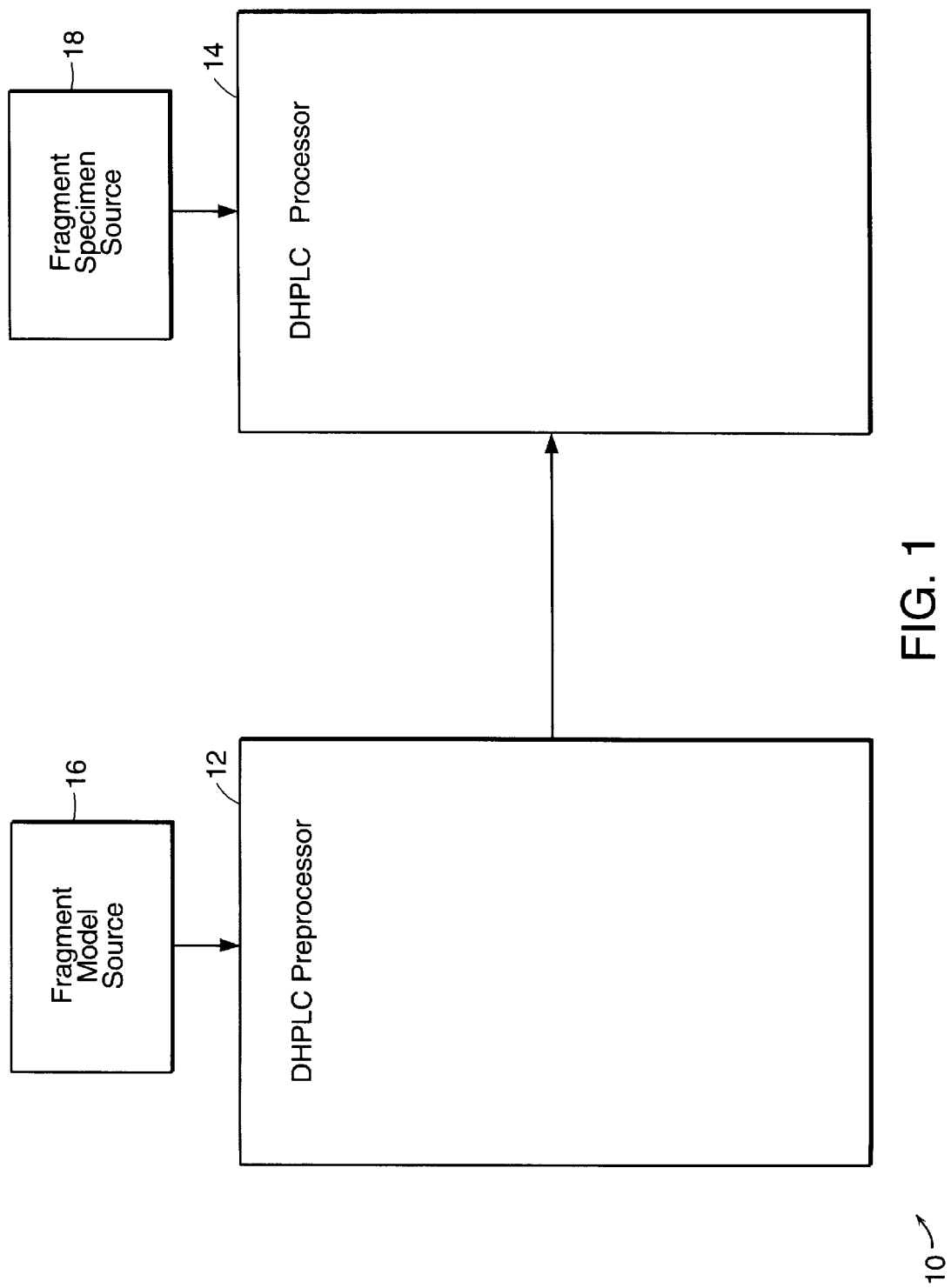
FIG. 1 is a block diagram of a DHPLC separation system.

FIG. 1 shows a preferred embodiment of a DHPLC separation system 10 according to the current invention. The DHPLC separation system 10 includes a DHPLC preprocessor 12 coupled, in series, to a DHPLC processor 14. Also shown are two DNA fragment sources, a fragment model source 16 and a fragment specimen source 18. The DNA fragment model source 16 provides input to the DHPLC preprocessor 12 and the DNA fragment specimen source 18 provides input to the DHPLC processor 14.

The DNA fragment model source 16 provides a DNA fragment to the DHPLC preprocessor 12 from which an operating temperature and a solution concentration are determined for the DHPLC processor 14. Specifically, a DNA sequence for the DNA fragment is provided. The DNA sequence is comprised of a unique combination of the letters A, C, T and G, representing the base pair order of the DNA fragment.

In response to the input DNA fragment sample, the solution preprocessor 12 calculates a corresponding acetonitrile solution concentration and operating temperature. This acetonitrile concentration and operating temperature determine the chromatography column percent acetronitrile solution and temperature for the DHPLC processor 14. Thus, on output, the preprocessor 12 provides the calculated threshold operating temperature and acetonitrile solution concentration.

In turn, the DHPLC processor 14 receives the operating temperature and acetonitrile solution concentration as output from the preprocessor 12 and operates the DHPLC processor 14 such as in the manner described in Underhill et al., "Detection of Numerous Y Chromosome Biallelic Polymorphisms by Denaturing High Performance Liquid Chromatography," *Genome Research*, p.1003 (1997) on a DNA fragment sample provided from the DNA fragment specimen source 18. It is understood that other similar DHPLC systems may be employed. On output, the DHPLC processor 14 provides an indication of a sequence mismatch possibly signifying a mutation of the given specimen DNA fragment.

It should be noted that the DHPLC preprocessor 12 may also be configured as a digital control unit for the DHPLC processor 14. In such a configuration, the testing environment of the DHPLC processor 14 may be automatically controlled. Automatic control of the testing environment reduces or eliminates operator error.

In addition, as a digital control unit for the DHPLC processor 14, the DHPLC preprocessor 12 provides an environment in which multiple DNA fragments may be analyzed in parallel. By eliminating a "trial and error" approach to temperature and solution concentration selection as well as providing parallel testing capability, a control system configuration for the DHPLC preprocessor 12 saves operator time. In addition, synchronization of sample testing may also be achieved.

Figure 2:
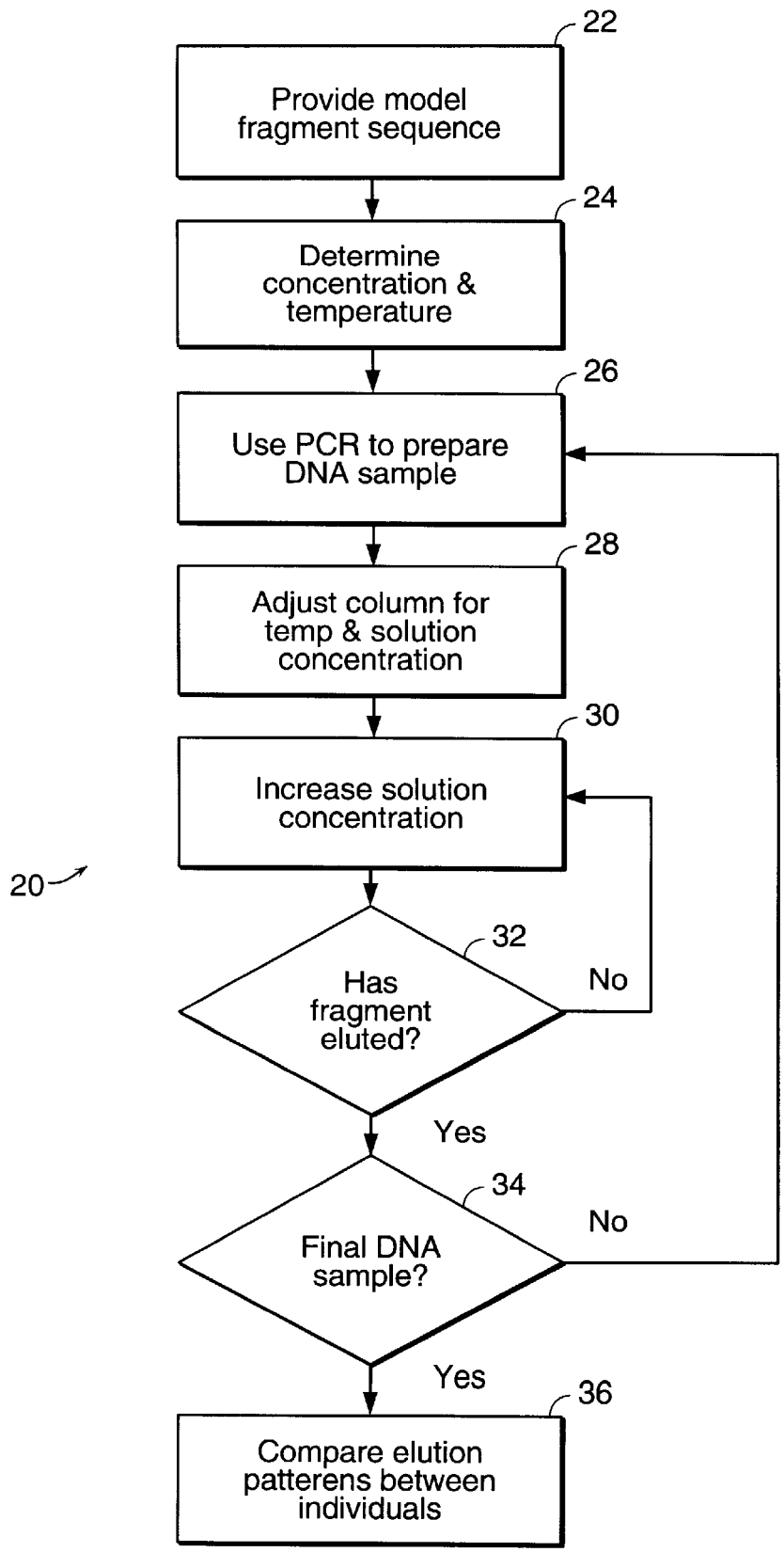
FIG. 2 is a flow diagram depicting the operation of the DHPLC separation system of FIG. 1.

Referring now to FIG. 2, a data flow chart and control diagram 20 is provided depicting the operation of the DHPLC separation system 10 of FIG. 1. Given a model DNA fragment and one or more sample DNA fragments, the DHPLC separation system 10 produces data, enabling an operator to discover mutations in the sample DNA.

At step 22, a model fragment sequence is provided to the DHPLC preprocessor 12 (FIG. 1). Typically, this sequence is a known quantity, serving as a standard to which sample DNA will be compared. Ideally, this model fragment includes no mutations.

At step 24, an acetonitrile solution concentration and operating temperature for the DHPLC processor 14 (FIG. 1) are calculated. These values are determined from the length of the model fragment as well as the actual sequence of the fragment as will be described in more detail below with reference to FIGS. 3 through 7.

It should be noted that, as described in the background, a desirable solution concentration and operating temperature for the DHPLC analysis must be specified. If too high a starting concentration is used, the fragment may be instantly removed from the column, eliminating any behavioral differences between removing a mutated fragment from the column and removing a non-mutated fragment.

Moreover, as described above, factors influencing the amount of solution required to remove the DNA fragment from the column include the length of the DNA fragment as well as the percent of the fragment which is separated or melted. If the operating temperature is too high, the strands of the DNA fragment will be completely separated, thus overstepping the critical temperature at which the strand separation for mutated fragments differs from non-mutated fragments. Subsequent application of the acetonitrile solution will remove mutated DNA fragments in a similar manner to non-mutated DNA fragments as both fragments would be completely separated. Consequently, eliminating any behavioral differences which may be observed to detect a mutation. Similarly, if the temperature is too low, no separation may occur, again making mutation detection difficult if not impossible.

At step 26, a DNA sample from an individual is prepared. Typically, a polymerase chain reaction (PCR) is used where multiple copies of a DNA fragment are produced, however any comparable technique to provide multiple duplicates of a DNA fragment may be used. Using PCR, a single sequence from a DNA sample is amplified and copies are made consisting of the single identified sequence.

At step 28, an analytic HPLC column is adjusted to the concentration of acetonitrile solution and temperature calculated in step 24. The DNA sample is injected onto the column, to which, the DNA sample adheres. As described in the background, applying heat to a DNA fragment will cause the strands of the fragment to separate or melt. Application of the acetonitrile solution to the DNA fragments on the HPLC column will tend to remove the fragments from the column.

The acetonitrile solution concentration is gradually increased at step 30. The increased concentration will eventually strip the DNA samples off the HPLC column. As the solution concentration is increased, the amount of DNA eluting off the column is monitored by an in-line detector at step 32. The data observed by the detector is stored for later reference. Typically, a final concentration for the acetonitrile solution is also determined. Until this final concentration is reached, the solution concentration is continually increase at step 30. Once the final solution concentration has been applied, the process proceeds to step 34.

At step 34, a check is made to determine whether this is the final DNA sample to be tested. If it is not, the procedure returns to step 26 where a DNA sample from another individual is prepared. Again, steps 28 through 34 are repeated until all samples have been prepared and tested.

It should be noted, as discussed above, in an instance where the DHPLC preprocessor 12 (FIG. 1) is operated as a digital control unit, step 34 may be eliminated, as multiple DNA samples may be tested in parallel. This particular embodiment would eliminate the time required to run a test for each individual in series.

At step 36, the final data is analyzed. Specifically, the pattern of elution of the DNA samples over time is compared to the DNA samples of each individual. Analysis of the data will show an amount of DNA being removed from the column by a lower concentration of the acetonitrile solution for individuals whose DNA sample has a mutation than for those individuals whose DNA sample does not have a mutation. That is, a DNA sample including a mutation will be removed from the column at a lower concentration of the acetonitrile solution because, at the operating temperature it would be more melted than a fragment without a mutation and less solution is required.

DNA analysis such as described above is used to identify mutations which have not previously been identified. In addition, this analysis is used in instances where a particular mutation has been identified and an individual is screened to determine whether he or she possesses the previously identified DNA mutation.

Figure 3:
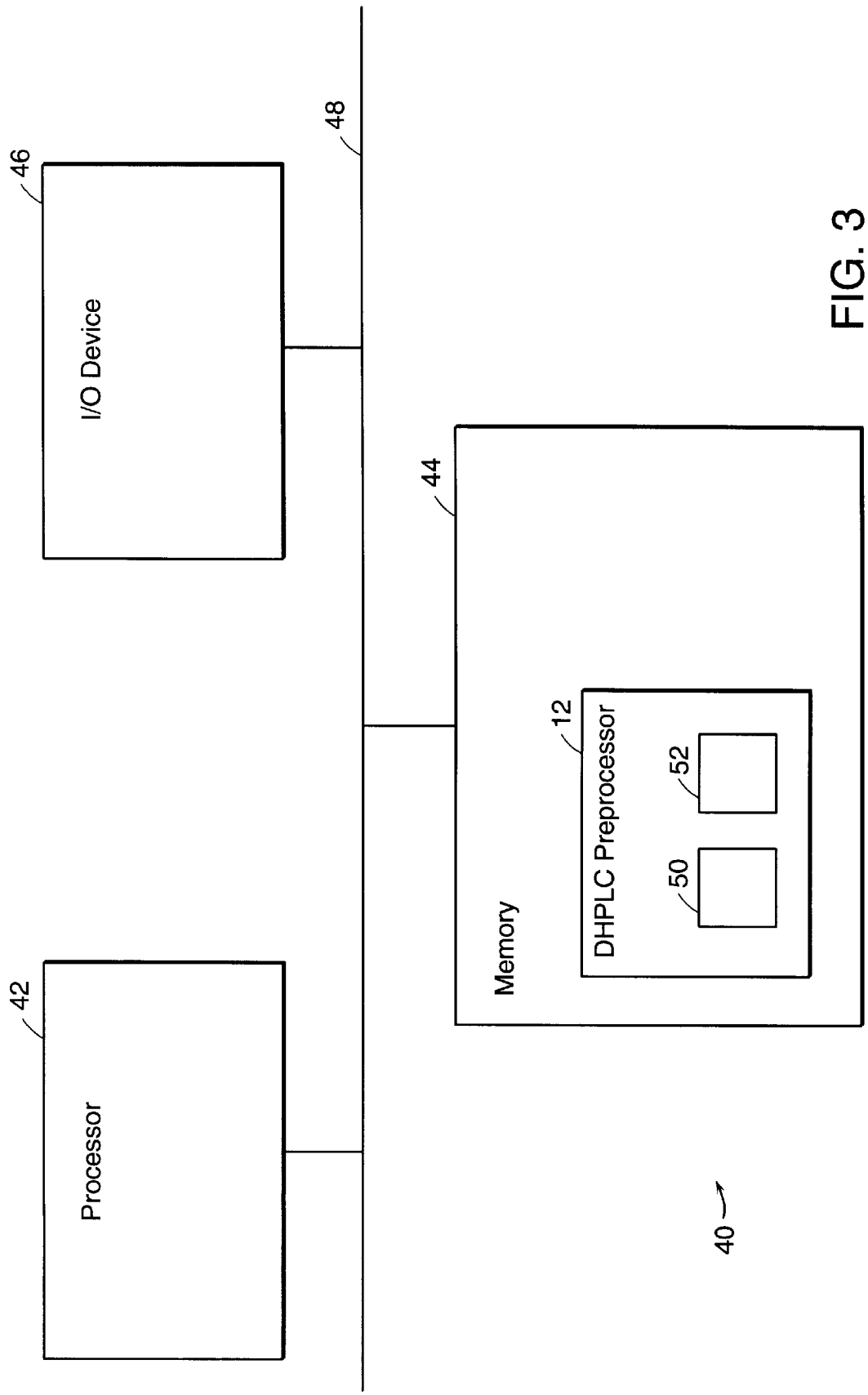
FIG. 3 is a block diagram of a preferred embodiment of the present invention.

FIG. 3 shows a general purpose computer 40 that is suitable for implementing the DHPLC preprocessor 12 of FIG. 1. The computer 40 includes a digital processor 42, a main memory 44, and an input/output (I/O) device 46, which are connected together electrically through a bus 48.

The main memory 44 includes the DHPLC preprocessor 12. The DHPLC preprocessor 12 includes a solution concentration module 50 and a temperature module 52. Here, the input/output device 46 includes the DNA fragment model source 16 which is operated by a user to provide a DNA fragment sequence to the DHPLC preprocessor 12. Alternative embodiments may be contemplated by one of skill in the art in which the DNA fragment model source 16 includes direct user input through a user interface, a database coupled through a network from a local server or alternatively an external server source, and the like.

Once the DNA fragment has been provided to the DHPLC preprocessor 12, the length of the fragment is determined. Typically, the length of the fragment is determined by counting the number of base pairs represented by the sequence string. The model fragment length is provided to the solution concentration module 50. The solution concentration module 50 determines a solution concentration to be used in the DHPLC process from the length value.

Figure 4:
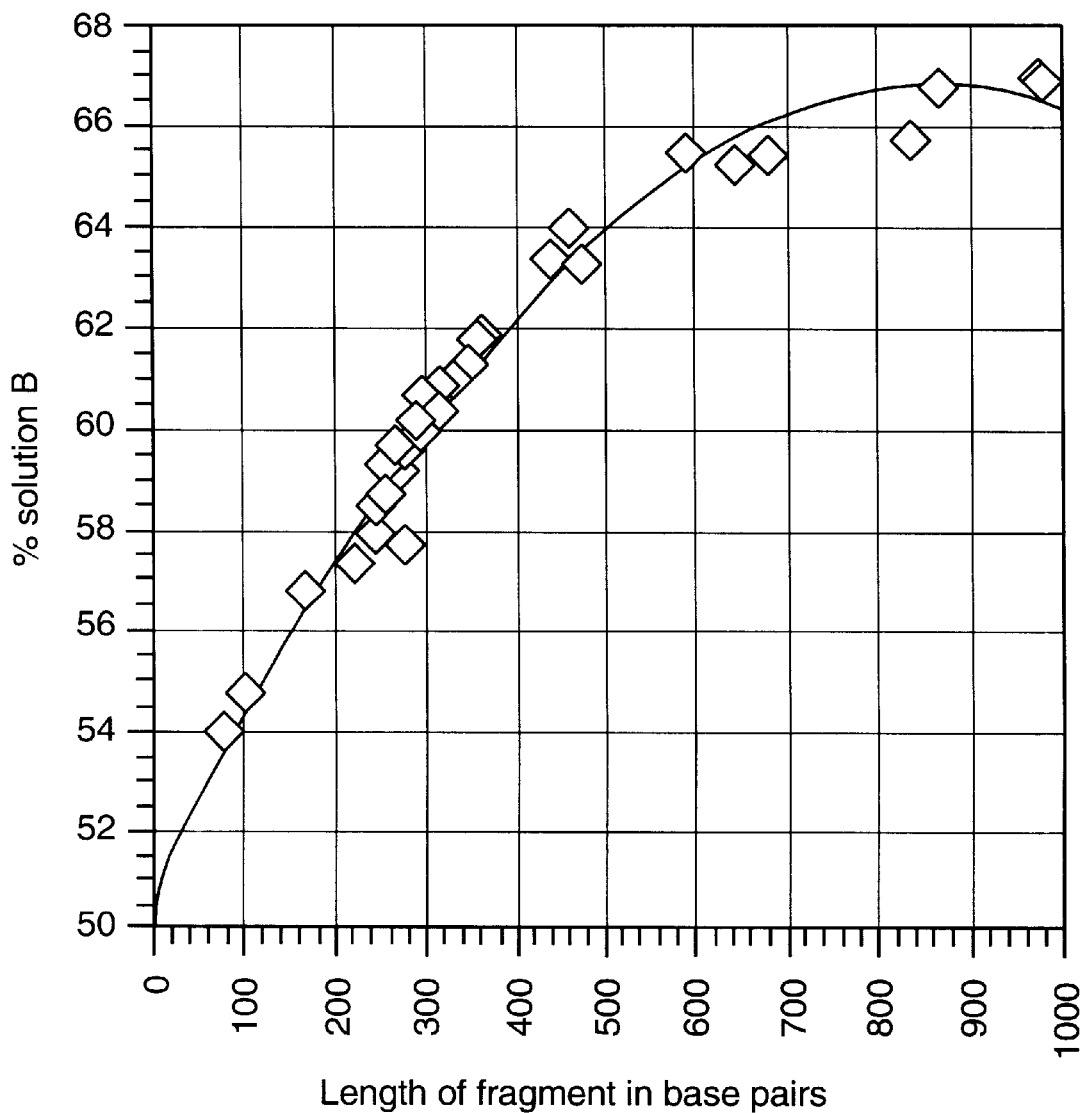
FIG. 4 is a graph illustrating the relationship between percent solution of acetonitrile and length of DNA fragment.

Specifically, a graph, similar to the one provided in FIG. 4, displays a relationship between the length of a DNA fragment and a solution concentration necessary to remove a DNA fragment from a chromatography column in a DHPLC process. The data on this graph was empirically generated. Applicants derived an equation representing the relationship which, given a DNA fragment length, yields a desirable solution concentration. For DNA fragments between 200 and 1000 base pairs in length, this equation is given as $\% \ C = 12.725 + 0.0092 \ L - 0.0000533 \ L^2$ where % C is the concentration of the solution solved as a percentage and L is the length of the DNA fragment in base pairs (bp).

The temperature module 52 is also provided the DNA model fragment sequence. From the fragment sequence, the temperature module 52 provides, at output, a temperature at which the DHPLC method may be operated to detect a mutation in a sample DNA fragment.

First, by way of background, gel electrophoresis separation of DNA fragments predates the liquid chromatography technique described above. The threshold temperature for Denaturing Gradient Gel Electrophoresis (DGGE) for purposes of strand separation may be determined by Melt94, a software program produced by Leonard Lerman. See web.mit.edu. Because the temperatures calculated by Melt94 are specific to gel eluted separation of DNA fragments, the temperature indicated on output of Melt94 is not directly usable by DHPLC systems/techniques.

Figure 5:
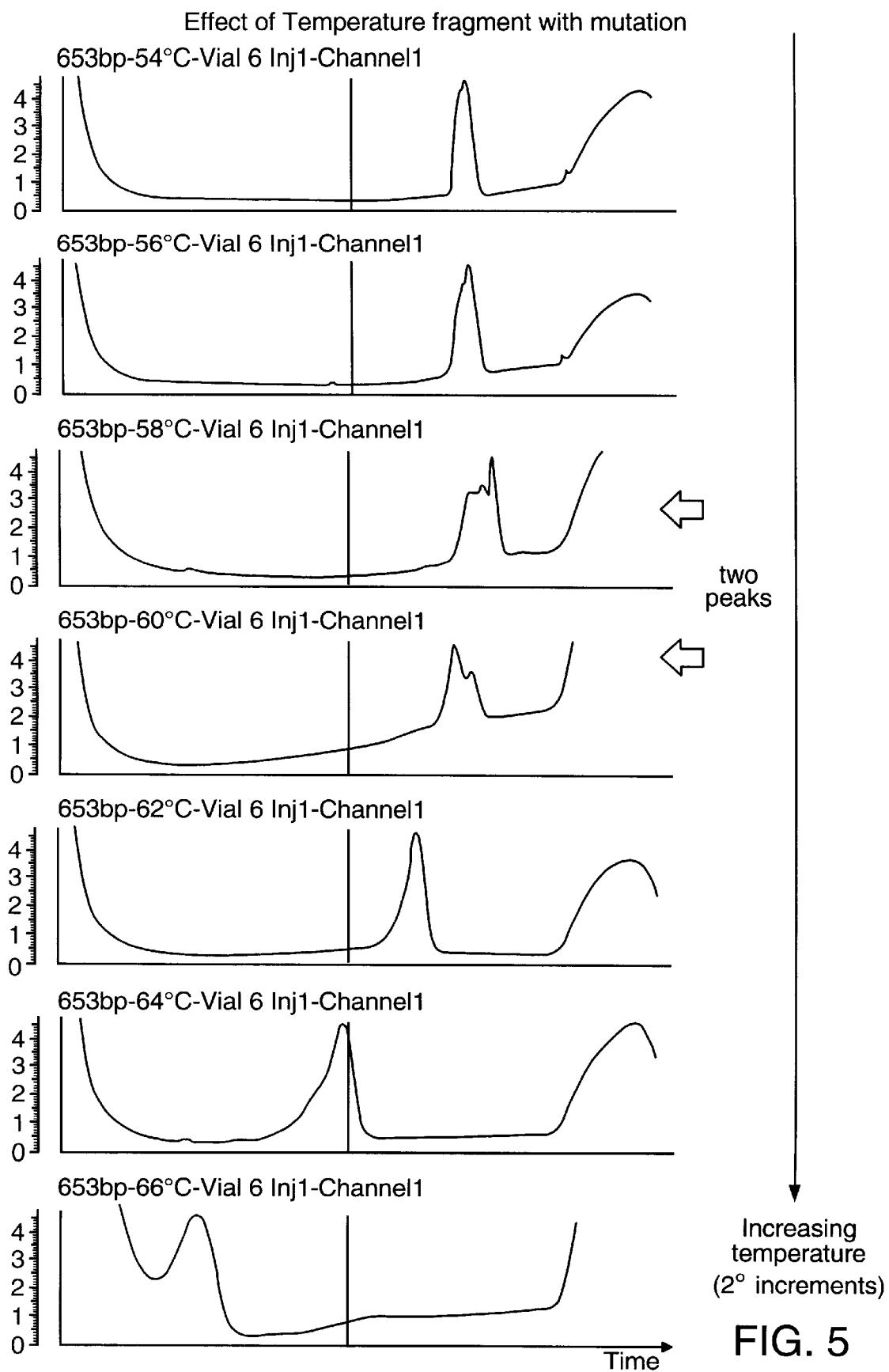
FIG. 5 is a graphical illustration of the effect of temperature on a DNA fragment with a mutation.

Applicant thus compared the temperatures calculated and output by Melt94 with observed melt temperatures for the same DNA fragment in a DHPLC environment. In particular, Applicant applied heat of increasing temperature to a subject DNA fragment and noted the temperatures at which mutations were observed as illustrated in FIG. 5. The mutations are indicated by two peaks as indicated in FIG. 5. The test conditions and temperature variance (e.g., increase by two degrees F. increments) was according to standards common in the art.

Figure 6:
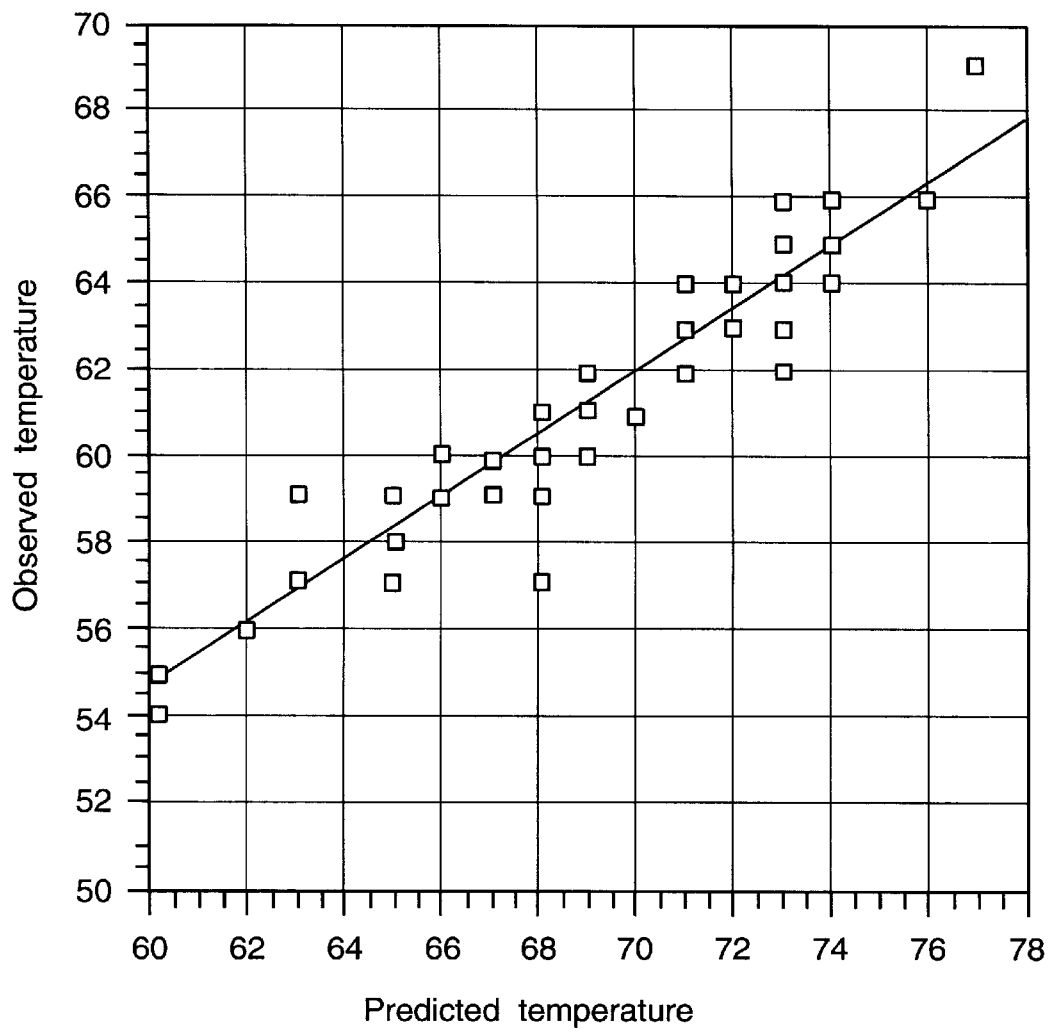
FIG. 6 is a graphical chart illustrating the relationship between predicted melting temperatures and observed melting temperatures of a subject DNA fragment.
Figure 7:
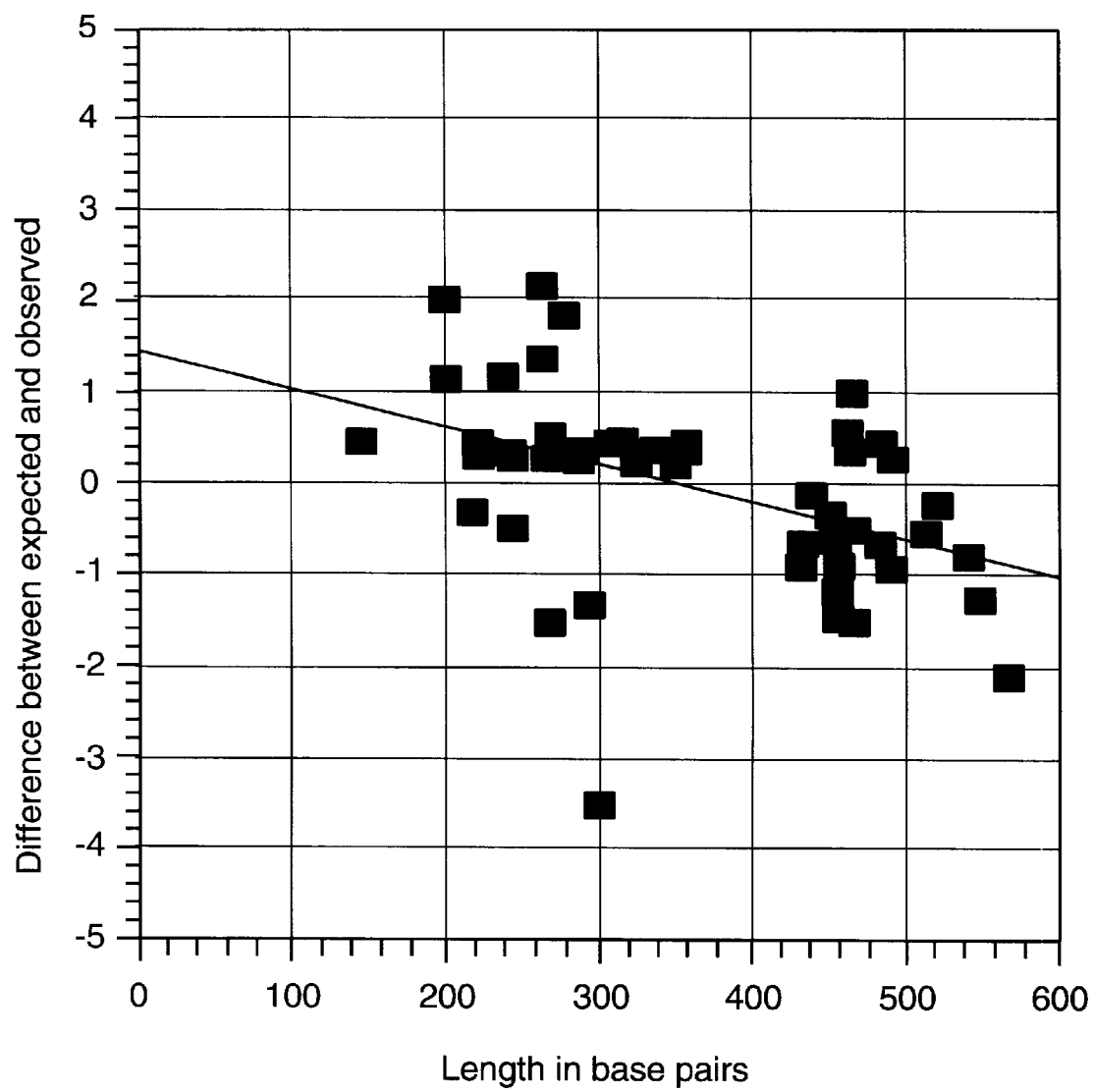
FIG. 7 is a graph illustrating the temperature dependency on DNA fragment melt temperature.

In comparing the Melt94 produced temperatures and the observed melting temperatures, Applicant generated the graph illustrated in FIG. 6. As a result, Applicant discovered a mathematical relationship between the Melt94 produced melt temperatures and the observed melting temperatures. Any errors in the mathematical relationship were accounted for, in part, by the length of the subject DNA fragment as illustrated in FIG. 7.

Based on the foregoing comparison study by the Applicant, Applicant has discovered that the desired threshold/operating temperature for DHPLC techniques is the temperature at which the subject DNA fragment is predicted 25 percent melted in the DGGE technique. Moreover, the resulting mathematical relationship may be expressed by the equation described threshold performance $T (° C.)=18.6+0.63 M-0.003 L$, where L is the length of the DNA fragment in base pairs and M is the desired operating temperature predicted by Melt94, the 25% melted temperature. Thus, the temperature module 52 of the preferred embodiment operates as follows and illustrated in FIG. 8.

Figure 8:
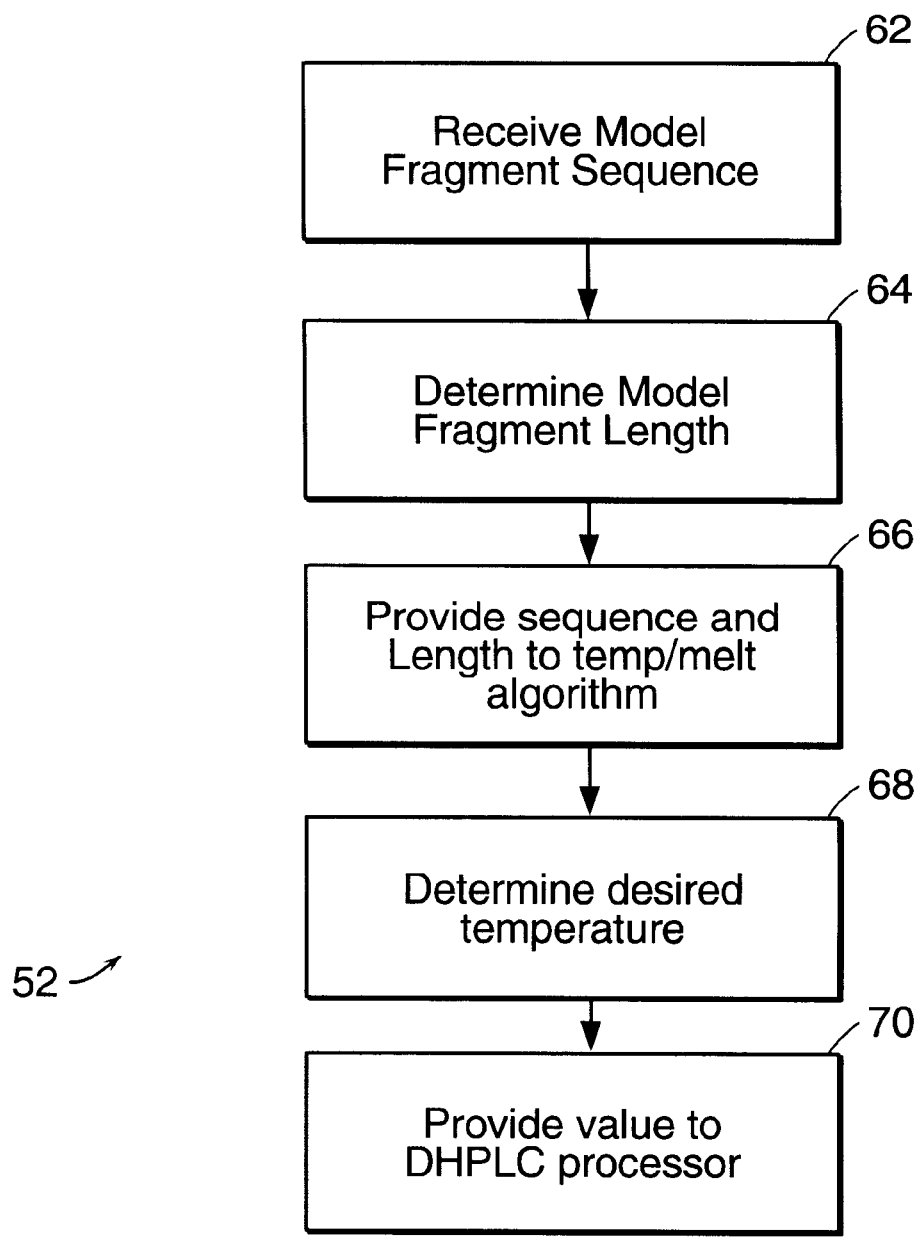
FIG. 8 is a flow diagram depicting the operation of the temperature module of FIG. 3.

Referring now to FIG. 8, the operation of the temperature module 52 begins at step 62 where the temperature module 52 receives on input, an indication of a DNA sequence or series of subject DNA sequences desired to be processed. The DNA sequence is a character string comprising a unique combination of the letters A, C, T and G, indicating the number and order of base pairs constituting the subject DNA fragment.

At step 64, the fragment length of the DNA fragment is determined. This is typically achieved by counting the number of base pairs represented in the DNA sequence as fragment length is usually provided in base pairs (bp). Alternatively, the length may also be provided directly from the fragment model source 16 or from the solution concentration module 50 which also requires this information.

At step 66, the DNA sequence and length values are provided to a temperature/melt algorithm for determining operating threshold temperatures for gel electrophoresis separation of DNA fragments such as described in Lerman L S, Silverstein K Methods Enzymol 1987;155:482–501 "Computational simulation of DNA melting and its application to denaturing gradient gel electrophoresis" which is herein incorporated by reference. The algorithm is described as "based largely on the algorithm of Fixman and Freire as a computationally practical approximation of Poland's sequence-specific, two-state theory of the helix-random chain transition."

In a preferred embodiment, the fragment sequence is formatted for use in Melt94, or other similar software, which incorporates the above-mentioned algorithm. As such, the temperature module 52 writes a control sequence to run said software (e.g., Melt94) using the reformatted input. The gel electrophoresis software (Melt94) is launched with the control sequence written from the reformatted input. On output, working software (Melt94) generates a series of files each with a plurality of temperature indications representing the predicted relationship between temperature and DNA melting.

From the gel electrophoresis software (Melt94) output file, the temperature module 52 extracts the temperature at which the subject DNA sequence is 25 percent melted. In particular, where n is the number of different letter elements in a single strand of the subject DNA sequence, the temperature module 52 extracts the temperature corresponding to n/4.

The operating temperature is calculated at step 68 by solving the equation $T (° C.)=18.6+0.63 M-0.003 L$, where L is the length of the DNA fragment in base pairs and M is the desired operating temperature predicted by Melt94, the 25% melted temperature results of step 66. This calculated, operating temperature value is provided, at output, to the DHPLC processor 14 at step 70.

It should be noted that, although software to determine an operating temperature for DNA fragment separation is available, little direction has been provided to assist an operator in selecting a temperature which is most desirable for identifying mutations in DNA fragments. For example, the Melt94 software described above provides, at output, a plurality of operating temperatures and the corresponding percent melted for a DNA fragment exposed to the temperature. Again, no direction is provided to assist the operator as to which temperature or percent melted state is most desirable for detecting mutations in a DNA fragment. In addition, the Melt94 software was developed for the gel electrophoresis technique and not the DHLPC technique. With regard to the DHPLC technique however, a website, is available (http://insertion.stanford.edu/melt.html) which, given a DNA sequence or multiple DNA sequences, provides an operating temperature for DHPLC analysis. Output from this website, however, has not proven useful in Applicants' studies, thus requiring undue experimentation to identify a desirable operating temperature.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein.

For example, various software for determining operating temperatures of gel electrophoresis separation of DNA fragments, whether for purposes of mutation detection or not, are suitable. One specific such software is described above as Melt94, for purposes of illustration and not limitation.

Further, the temperature corresponding to a 25% melted level is discussed above in the preferred embodiment. Temperatures corresponding to other similar percent melted levels may be of interest. Thus a range (e.g., 20%–30% melted) of percent melted including 25% is suitable for carrying out the intent of the present invention.

What is claimed is:

1. A method for determining the existence of a DNA mutation in a first DNA fragment comprising the steps of:
   providing a second DNA fragment, the first DNA fragment and second DNA fragment each being double stranded;
   using a digital processor, calculating for use in a second testing environment (i) an operating temperature, at which strands of the second DNA fragment become partially separated, the operating temperature being derived from a threshold temperature calculated for a sequence of the second DNA fragment in a first testing environment, and (ii) a concentration of a working solution used in the second testing environment to apply to the first DNA fragment, the first and second testing environments being different separation processes;
   exposing the first DNA fragment to the second testing environment, using the calculated operating temperature and calculated solution concentration; and
   contrasting the behavior of the first DNA fragment in the second testing environment with an expected behavior of the second DNA fragment in the second test environment.

2. The method of claim 1 wherein the step of providing the second DNA fragment includes the step of:
   providing, to the digital processor, a DNA sequence comprising a unique combination of the code letters A, C, T and G.

3. The method of claim 1 wherein the step of providing a second DNA fragment further includes the step of:
   using a polymerase chain reaction to provide multiple copies of a sample DNA fragment.

4. The method of claim 1 wherein the first testing environment employs a gel electrophoresis method for DNA strand separation and the second testing environment employs a Denaturing High Performance Liquid Chromatography technique.

5. The method of claim 4 wherein the step of calculating operating temperature includes calculating operating temperature at which 25% separation of the strands of the second DNA fragment occurs.

6. The method of claim 5 wherein the step of calculating an operating temperature T includes solving the equation $T=18.6+0.63\ M-0.003\ L$, where M is the calculated threshold temperature and L is a length of the second DNA fragment in base pairs, the calculated threshold temperature being a function of temperature at which the strands of the second DNA fragment are about 25% separated in the gel electrophoresis method.

7. The method of claim 4 wherein the step of calculating a solution concentration includes solving the equation $\%\ C=12.725+0.0092\ L-0.0000533\ L^2$, where L is the length of the second DNA fragment in base pairs.

8. The method of claim 7 wherein the solution is acetonitrile.

9. The method of claim 8 wherein the step of exposing the first DNA fragment includes:
   increasing a solution concentration from the calculated solution concentration until the first DNA fragment is completely removed from an HPLC column; and
   recording an elution rate of the strands of the first DNA fragment in response to the step of increasing the solution concentration.

10. The method of claim 9 wherein the step of contrasting includes the step of:
    comparing the elution rate of the strands of the first DNA fragment in the second testing environment to an expected elution rate of the strands of the second DNA fragment in the second testing environment.

11. A DHPLC preprocessor for providing an operating temperature and a solution concentration for an analytic DHPLC column, comprising:
    a DNA sequence means for receiving sequences indicative of respective DNA fragments;
    an operating temperature component coupled to the DNA sequence means and receiving a sequence indicative of a subject DNA fragment, the operating temperature component calculating an operating temperature based on gel electrophoresis threshold temperature at which strands of the subject DNA fragment become partially separated; and
    a solution concentration component coupled to the DNA sequence means, for calculating the solution concentration at which the subject DNA fragment is removed from the analytic DHPLC column.

12. The DHPLC preprocessor of claim 11 wherein the operating temperature component further includes:
    a threshold temperature component for calculating the gel electrophoresis threshold temperature at which strands of the subject DNA fragment become 25% separated in a gel electrophoresis testing environment.

13. The DHPLC preprocessor of claim 12 wherein the operating temperature component further includes:
    a temperature conversion component for deriving the operating temperature (T) from the threshold temperature (M) using the equation $T=18.6+0.63\ M-0.003\ L$, where L is a length, in base pairs, of the subject DNA fragment.

14. An apparatus comprising:
    machine executable code for a method of calculating an operating temperature and acetonitrile solution concentration for a DHPLC process including the steps of;
    deriving, from a threshold temperature calculated for a gel electrophoresis process, the operating temperature at which strands of a DNA fragment become partially separated; and
    calculating a concentration of a solution for the DHPLC process; from an input comprising a DNA fragment sequence.

* * * * *